United States Patent
Park et al.

(10) Patent No.: US 9,540,374 B2
(45) Date of Patent: Jan. 10, 2017

(54) NITROGEN-CONTAINING HETEROCYCLIC COMPOUNDS AND ORGANIC ELECTRONIC DEVICE COMPRISING THE SAME

(71) Applicant: LG CHEM, LTD., Seoul (KR)

(72) Inventors: Tae Yoon Park, Daejeon (KR);
Dongheon Kim, Daejeon (KR);
Minseung Chun, Daejeon (KR);
Hyoung Seok Kim, Daejeon (KR);
Jiyeon Ahn, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/419,589

(22) PCT Filed: Apr. 22, 2014

(86) PCT No.: PCT/KR2014/003492
§ 371 (c)(1),
(2) Date: Feb. 4, 2015

(87) PCT Pub. No.: WO2014/175627
PCT Pub. Date: Oct. 30, 2014

(65) Prior Publication Data
US 2015/0218163 A1  Aug. 6, 2015

(30) Foreign Application Priority Data

Apr. 22, 2013 (KR) .................. 10-2013-0044498

(51) Int. Cl.
*C07D 471/10* (2006.01)
*H01L 51/00* (2006.01)
(Continued)

(52) U.S. Cl.
CPC ............. *C07D 471/10* (2013.01); *C09K 11/06* (2013.01); *H01L 51/0072* (2013.01); *C09K 2211/1011* (2013.01); *C09K 2211/1029* (2013.01); *H01L 51/0052* (2013.01); *H01L 51/0058* (2013.01); *H01L 51/0508* (2013.01); *H01L 51/0512* (2013.01); *H01L 51/42* (2013.01); *H01L 51/5012* (2013.01); *H01L 51/5056* (2013.01);
(Continued)

(58) Field of Classification Search
None
See application file for complete search history.

(56) References Cited

U.S. PATENT DOCUMENTS

2006/0113905 A1* 6/2006 Nakamura .......... H01L 27/3244
313/511
2007/0247059 A1  10/2007 Cho et al.
(Continued)

FOREIGN PATENT DOCUMENTS

CN  101010409 A  8/2007
JP  2008-510800 A  4/2008
(Continued)

OTHER PUBLICATIONS

Machine English translation of KR 1020120015883, Sep. 14, 2015.*
Machine English translation of KR 10-2006-0051606, Nov. 28, 2015.*

*Primary Examiner* — J. L. Yang
(74) *Attorney, Agent, or Firm* — Dentons US LLP

(57) ABSTRACT

The present invention provides a nitrogen-containing heterocyclic compound and an organic electronic device including the same.

16 Claims, 5 Drawing Sheets

(51) Int. Cl.
  *C09K 11/06* (2006.01)
  *H01L 51/05* (2006.01)
  *H01L 51/42* (2006.01)
  *H01L 51/50* (2006.01)
  *H01L 51/52* (2006.01)
  *H01L 51/56* (2006.01)

(52) U.S. Cl.
  CPC ...... *H01L 51/5072* (2013.01); *H01L 51/5088* (2013.01); *H01L 51/5092* (2013.01); *H01L 51/5203* (2013.01); *H01L 51/56* (2013.01); *H01L 2251/301* (2013.01); *H01L 2251/308* (2013.01); *Y02E 10/549* (2013.01); *Y02P 70/521* (2015.11)

(56) References Cited

U.S. PATENT DOCUMENTS

2011/0278549 A1  11/2011  Kim et al.
2014/0138670 A1   5/2014  Nakagawa et al.

FOREIGN PATENT DOCUMENTS

| JP | 2009-073803 A | 4/2009 | |
|----|---|---|---|
| JP | 5110198 B1 | 12/2012 | |
| KR | 10-2006-0051606 * | 5/2006 | ............ C09K 11/06 |
| KR | 1020060051606 | 5/2006 | |
| KR | 1020070063354 | 6/2007 | |
| KR | 1020110053114 | 5/2011 | |
| KR | 1020120015883 * | 2/2012 | ............ H01L 51/50 |
| WO | 2006/080640 A1 | 8/2006 | |
| WO | 2013/011954 A1 | 1/2013 | |

* cited by examiner

NITROGEN-CONTAINING HETEROCYCLIC COMPOUNDS AND ORGANIC ELECTRONIC DEVICE COMPRISING THE SAME

TECHNICAL FIELD

This application is a 35 USC §371 National Stage entry of International Application No. PCT/KR2014/003492, filed on Apr. 22, 2014, which claims priority to and the benefit of Korean Patent Application No. 10-2013-0044498 filed in the Korean Intellectual Property Office on Apr. 22, 2013, the entire contents of which are incorporated herein by reference.

The present specification relates to a novel nitrogen-containing heterocyclic compound and an organic electronic device including the same.

BACKGROUND ART

An organic electronic device means a device requiring exchanging of electric charges between an electrode using holes and/or electrons and an organic material. The organic electronic device may be largely divided into the following two types according to an operation principle. A first type is an electric device in which an exciton is formed in an organic material layer by a photon flowing from an external light source to the device, the exciton is separated into an electron and a hole, and the electron and the hole are transferred to the different electrodes to be used as a current source (voltage source). A second type is an electronic device in which holes and/or electrons are injected into an organic material semiconductor forming an interface together with the electrode by applying a voltage or a current to two or more electrodes, and the electronic device is operated by the injected electrons and holes.

Examples of the organic electronic device include an organic light emitting device, an organic solar cell, an organic photoconductor (OPC), an organic transistor, and the like, and all of the examples require a hole injection or transport material, an electron injection or transport material, or a light emitting material in order to drive the device. Hereinafter, an organic light emitting device will be mainly described in detail, but in the organic electronic devices, the hole injection or transport material, the electron injection or transport material, or the light emitting material is operated based on the similar principle.

In general, an organic light emitting phenomenon means a phenomenon where electric energy is converted into light energy by using an organic material. The organic light emitting device using the organic light emitting phenomenon has a structure generally including an anode, a cathode, and an organic material layer interposed therebetween. Herein, in many cases, the organic material layer has a multilayered structure constituted by different materials in order to increase efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, the holes are injected from the anode to the organic material layer and the electrons are injected from the cathode to the organic material layer, and when the injected holes and electrons meet each other, an exciton is formed, and light is emitted when the exciton falls to a bottom state again. It is known that this organic light emitting device has properties such as self light emission, high brightness, high efficiency, a low driving voltage, a wide viewing angle, a high contrast, and a high speed response property.

In the organic light emitting device, the material used as the organic material layer may be classified into a light emitting material and an electric charge transport material, for example, a hole injection material, a hole transport material, an electron transport material, an electron injection material, and the like, according to a function thereof. Further, the light emitting material may be classified into blue, green, and red light emitting materials and yellow and orange light emitting materials required in order to implement better natural colors according to a light emitting color. Meanwhile, in the case where only one material is used as the light emitting material, since there are problems in that a maximum light emitting wavelength moves to a long wavelength or color purity is lowered due to interaction between molecules or efficiency of the device is reduced due to a reduced effect of light emission, host/dopant systems may be used as the light emitting material in order to increase the color purity and increase light emitting efficiency through transference of energy.

In order to sufficiently show the aforementioned excellent properties of the organic light emitting device, support of a material forming the organic material layer in the device, for example, the hole injection material, the hole transport material, the light emitting material, the electron transport material, the electron injection material, and the like with stable and efficient materials should be previously performed, but development of a stable and efficient material of an organic material layer for an organic light emitting device has not yet been sufficiently made. Therefore, there is a continuous demand for developing a novel material, and the necessity for developing the novel material is similarly applied to aforementioned other organic electronic devices.

PRIOR ART DOCUMENT

Patent Document

Korean Patent Application Laid-Open No. 10-2006-0051606

DETAILED DESCRIPTION OF THE INVENTION

Technical Problem

The present inventors found a nitrogen-containing heterocyclic compound having a novel structure. Further, the present inventors found the fact that an organic material layer of an organic electronic device can be formed to include the novel nitrogen-containing heterocyclic compound.

The present specification has been made in an effort to provide a nitrogen-containing heterocyclic compound and an organic electronic device including the same.

Technical Solution

An exemplary embodiment of the present invention provides a nitrogen-containing heterocyclic compound represented by the following Chemical Formula 1.

[Chemical Formula 1]

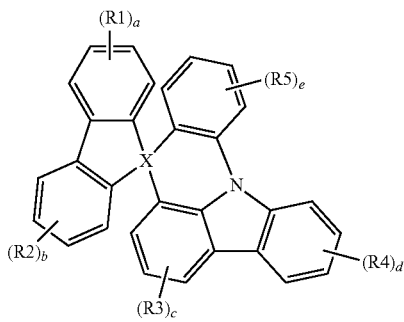

Wherein Chemical Formula 1,

X is C or Si, at least one of R1 and R2 is each independently represented by -L-A, L is a direct bond; or a divalent group including one kind or more selected from the group consisting of a substituted or unsubstituted aromatic cycle group and a substituted or unsubstituted heterocyclic group, A is a cyano group (—CN), R3 to R5, and a rest of R1 and R2 are each independently selected from the group consisting of hydrogen; deuterium; a halogen group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heterocyclic group including one or more of N, O, and S atoms, a, b, d, and e are each independently an integer of 1 to 4, and c is an integer of 1 to 3.

Another exemplary embodiment of the present invention provides an organic electronic device including: a first electrode; a second electrode facing the first electrode; and one or more organic material layers disposed between the first electrode and the second electrode, in which one or more of the organic material layers include the nitrogen-containing heterocyclic compound.

Yet another exemplary embodiment of the present invention provides a method of manufacturing an organic electronic device, including: preparing a substrate; forming a first electrode on the substrate; forming an organic material layer including the nitrogen-containing heterocyclic compound on the first electrode; and forming a second electrode on the organic material layer.

Advantageous Effects

According to the exemplary embodiment of the present specification, the nitrogen-containing heterocyclic compound may be used as a material of the organic material layer of the organic electronic device including the organic light emitting device.

According to the exemplary embodiment of the present specification, the nitrogen-containing heterocyclic compound has excellent thermal stability.

According to the exemplary embodiment of the present specification, the nitrogen-containing heterocyclic compound has a deep HOMO level.

According to the exemplary embodiment of the present specification, the nitrogen-containing heterocyclic compound has a high triplet state.

According to the exemplary embodiment of the present specification, the nitrogen-containing heterocyclic compound has high hole stability.

According to the exemplary embodiment of the present specification, the nitrogen-containing heterocyclic compound may be purely used or used while being mixed with an impurity in the organic electronic device including the organic light emitting device.

According to the exemplary embodiment of the present specification, the organic electronic device including the nitrogen-containing heterocyclic compound exhibits an excellent characteristic in terms of efficiency.

According to the exemplary embodiment of the present specification, the organic electronic device including the nitrogen-containing heterocyclic compound exhibits an excellent characteristic in terms of driving voltage.

According to the exemplary embodiment of the present specification, the organic electronic device including the nitrogen-containing heterocyclic compound exhibits an excellent life-span characteristic.

According to the exemplary embodiment of the present specification, the organic electronic device including the nitrogen-containing heterocyclic compound may have improved light efficiency.

According to the exemplary embodiment of the present specification, the organic electronic device including the nitrogen-containing heterocyclic compound may improve a life-span characteristic of the device.

EXPLANATION OF REFERENCE NUMERALS AND SYMBOLS

Figure 1:
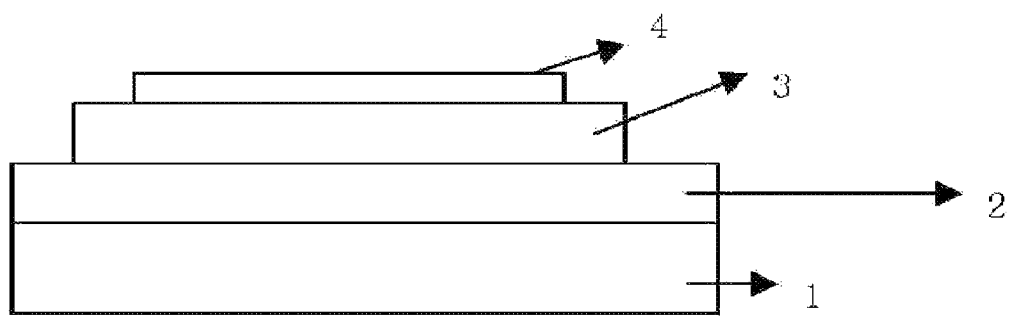
FIG. 1 illustrates an example of an organic light emitting device formed of a substrate 1, an anode 2, a light emitting layer 3, and a cathode 4.
Figure 2:
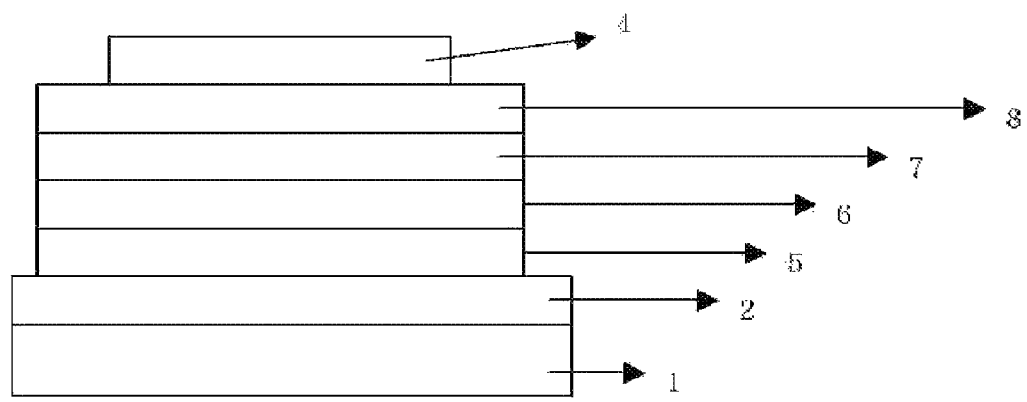
FIG. 2 illustrates an example of an organic light emitting device formed of a substrate 1, an anode 2, a hole injection layer 5, a hole transport layer 6, a light emitting layer 7, an electron transport layer 8, and a cathode 4.

1: Substrate
2: Anode 3, 7: Light emitting layer
4: Cathode
5: Hole injection layer
6: Hole transport layer
8: Electron transport layer

BEST MODE

Hereinafter, the present specification will be described in more detail.

According to an exemplary embodiment of the present specification, there is provided a nitrogen-containing heterocyclic compound represented by Chemical Formula 1.

Further, according to the exemplary embodiment of the present specification, the nitrogen-containing heterocyclic compound represented by Chemical Formula 1 may be a nitrogen-containing heterocyclic compound represented by any one of the following Chemical Formulas 1-1 to 1-5.

[Chemical Formula 1-1]

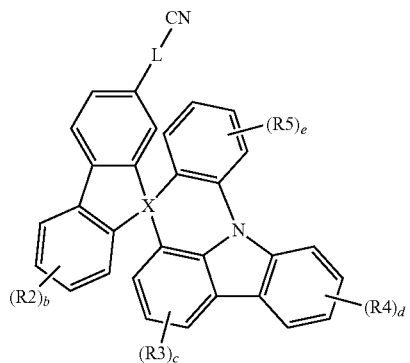

[Chemical Formula 1-2]

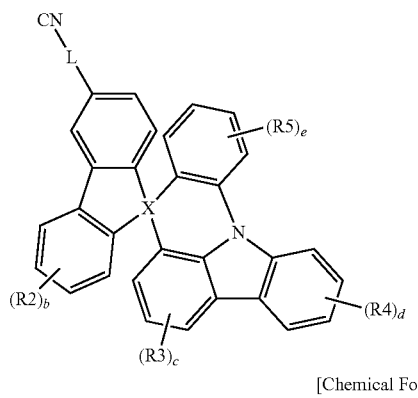

[Chemical Formula 1-3]

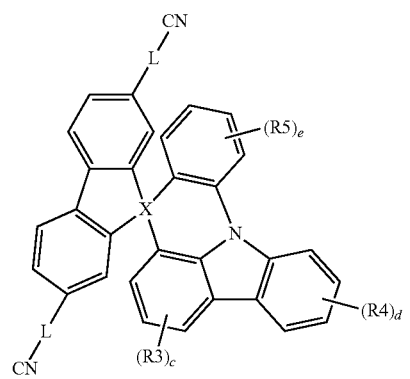

[Chemical Formula 1-4]

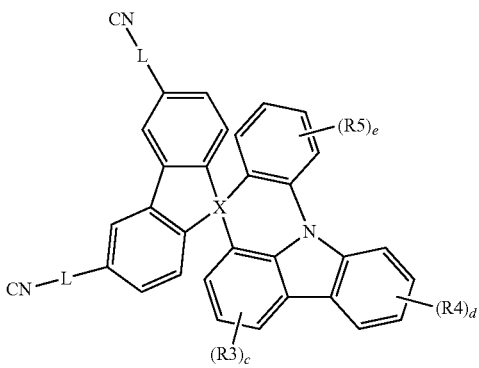

[Chemical Formula 1-5]

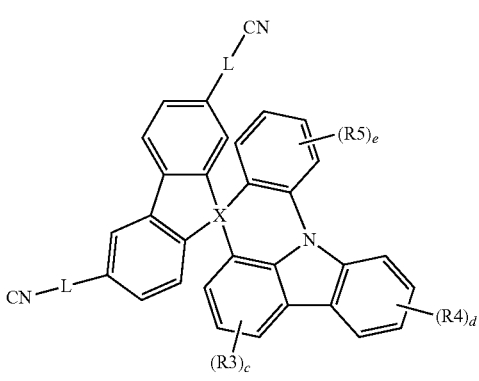

Wherein Chemical Formulas 1-1 to 1-5,

X is C or Si,

L is a direct bond; or a divalent group including one kind or more selected from the group consisting of a substituted or unsubstituted aromatic cycle group and a substituted or unsubstituted heterocyclic group, R2 to R5 are each independently selected from the group consisting of hydrogen; deuterium; a halogen group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heterocyclic group including one or more of N, O, and S atoms, b, d, and e are each independently an integer of 1 to 4, and c is an integer of 1 to 3.

In the present specification,

means a portion bonded to another substituent group or a bonding portion.

In the present specification, the term "substituted or unsubstituted" means that substitution is performed by one or more substituent groups selected from the group consisting of deuterium; a halogen group; an alkyl group; an alkenyl group; an alkoxy group; a cycloalkyl group; a silyl group; an arylalkenyl group; an aryl group; an aryloxy group; an alkylthioxy group; an alkylsulfoxy group; an arylsulfoxy group; a boron group; an alkylamine group; an aralkylamine group; an arylamine group; a heteroaryl group; a carbazole group; an arylamine group; an arylalkyl group; a fluorenyl group; a nitrile group; a thiol group; an alkylthio group; an allylthio group; a sulfoxy group; an acetylene group; a nitro group; a hydroxy group, and a heterocyclic group including one or more of N, O, S atoms, or there is no substituent group.

In the present specification, the "heterocyclic group" is a heterocyclic group including one or more of O, N and S atoms as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, examples of a "halogen group" include fluorine, chlorine, bromine, or iodine.

In the present specification, the "alkyl group" may be a straight or branched chain, and the number of carbon atoms thereof is not particularly limited but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohectylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the "cycloalkyl group" is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the "alkenyl group" may be a straight or branched chain, and the number of carbon atoms thereof is not particularly limited but is preferably 2 to 40. Specific examples thereof include vinyl, 1-prophenyl, isoprophenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the "alkoxy group" may be a straight, branched, or cyclic chain. The number of carbon atoms of the alkoxy group is not particularly limited, but preferably 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the "aryl group", which is an organic radical derived from aromatic hydrocarbons by removing one hydrogen, may be a monocyclic type or a polycyclic type, and the number of carbon atoms thereof is not particularly limited but is preferably 6 to 60. Specific examples of the aryl group include monocyclic aromatics such as a phenyl group, a biphenyl group, and a terphenyl group, polycyclic aromatics such as a naphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, and a fluoranthene group, and the like, but are not limited thereto.

In the present specification, the "fluorenyl group" has a structure where two cyclic organic compounds are connected through one atom, and examples thereof include

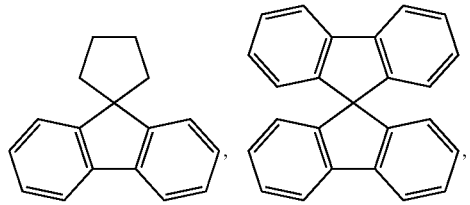

and the like.

In the present specification, the fluorenyl group includes a structure of an opened fluorenyl group, in which the opened fluorenyl group has a structure where two cyclic compounds are connected through one atom and connection of one cyclic compound is broken, and examples thereof include

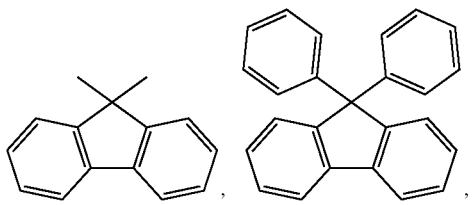

and the like.

In the present specification, examples of the "arylamine group" include a substituted or unsubstituted monocyclic monoarylamine group, a substituted or unsubstituted monocyclic monoarylamine group, a substituted or unsubstituted monocyclic diarylamine group, a substituted or unsubstituted monocyclic triarylamine group, a substituted or unsubstituted polycyclic diarylamine group, a substituted or unsubstituted polycyclic triarylamine group, substituted or unsubstituted monocyclic and polycyclic diarylamine groups, or substituted or unsubstituted monocyclic and polycyclic triarylamine groups. Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, the "terphenyl group" may be represented by the following substituent group. Further, carbon of the following terphenyl group may be substituted or unsubstituted carbon.

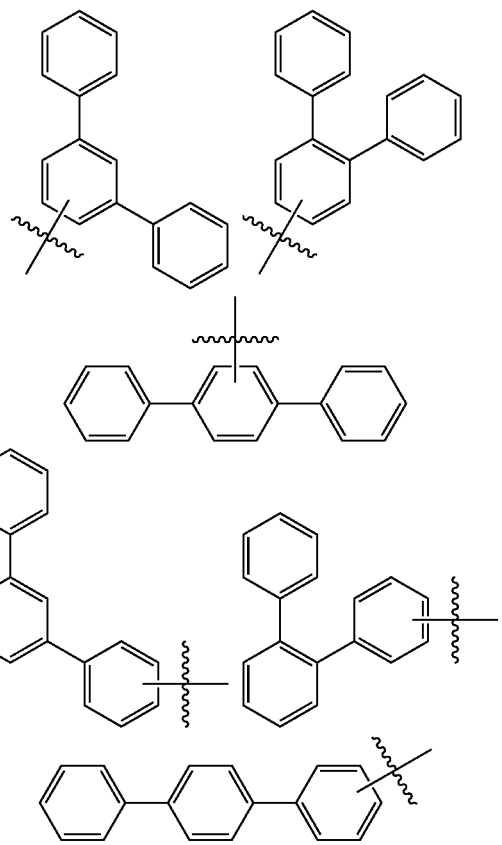

In the present specification, the "phenanthrene group" may be represented by the following substituent group. Further, carbon of the following phenanthrene group may be substituted or unsubstituted carbon.

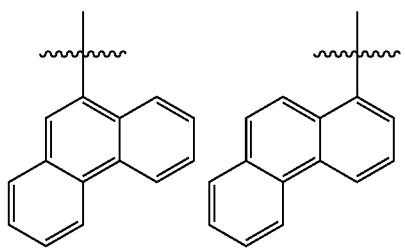

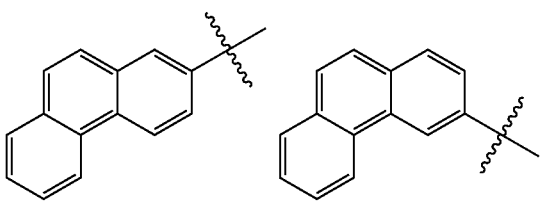

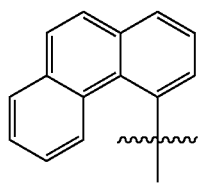

According to the exemplary embodiment of the present specification, L may be a substituted or unsubstituted phenylene group. Specifically, the substituted or unsubstituted phenylene group may be represented as below, and carbon of the phenylene group may be substituted or unsubstituted carbon.

According to the exemplary embodiment of the present specification, L may be a substituted or unsubstituted divalent phenylene group. Specifically, the substituted or unsubstituted divalent phenylene group may be represented as below, and carbon of the phenylene group may be substituted or unsubstituted carbon.

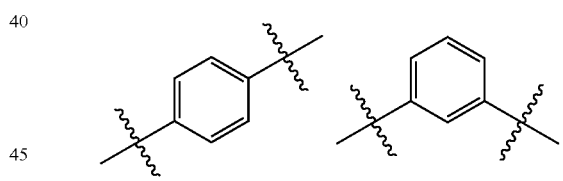

According to the exemplary embodiment of the present specification, L may be a substituted or unsubstituted divalent biphenyl group. Specifically, the substituted or unsubstituted divalent biphenyl group may be represented as below, and carbon of the biphenyl group may be substituted or unsubstituted carbon.

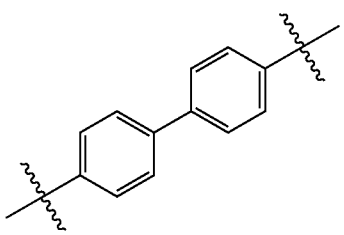

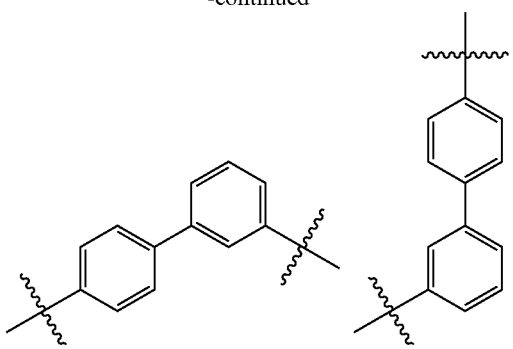

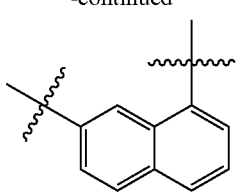

According to the exemplary embodiment of the present specification, L may be a substituted or unsubstituted divalent anthracene group. Specifically, the substituted or unsubstituted divalent anthracene group may be represented as below, and carbon of the anthracene group may be substituted or unsubstituted carbon.

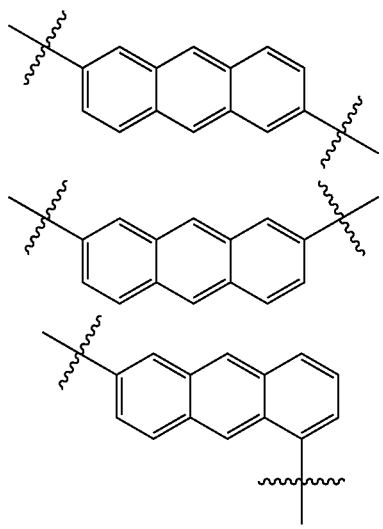

According to the exemplary embodiment of the present specification, L may be a substituted or unsubstituted divalent naphthalene group. Specifically, the substituted or unsubstituted divalent naphthalene group may be represented as below, and carbon of the naphthalene group may be substituted or unsubstituted carbon.

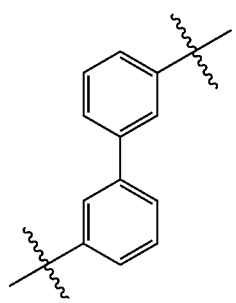

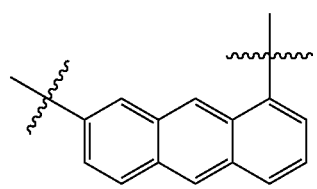

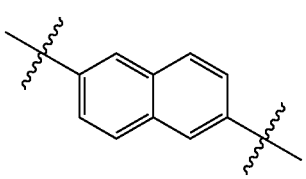

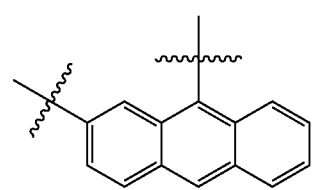

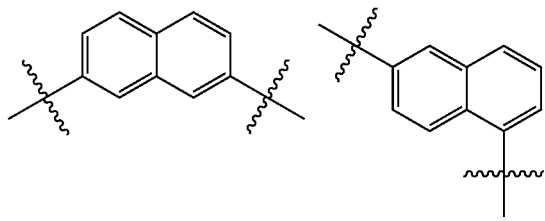

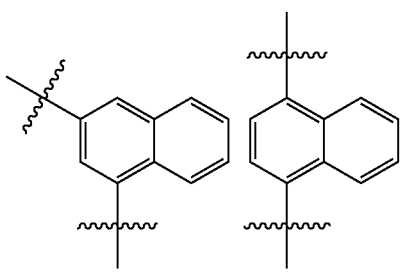

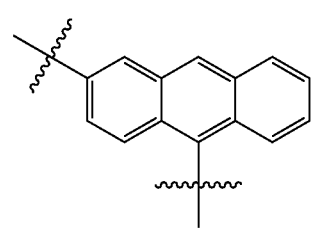

-continued

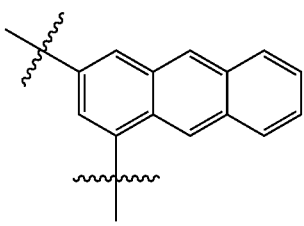

According to the exemplary embodiment of the present specification, L may be a substituted or unsubstituted divalent fluorene group. Specifically, the substituted or unsubstituted divalent fluorene group may be represented as below, and carbon of the fluorene group may be substituted or unsubstituted carbon.

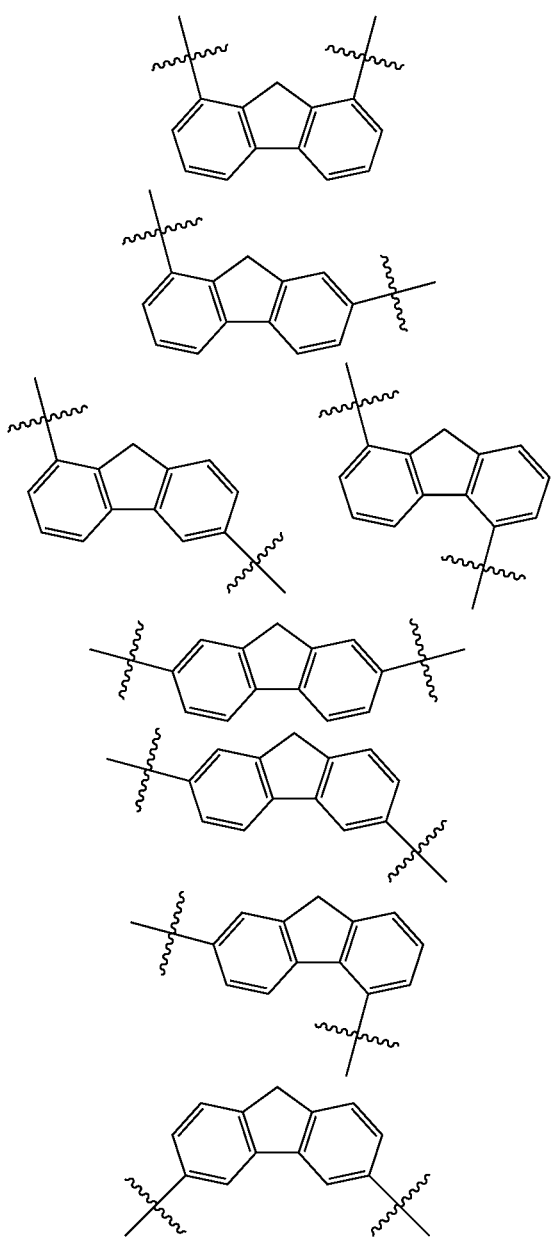

-continued

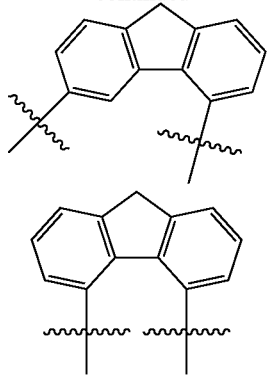

Further, according to the exemplary embodiment of the present specification, L may be a direct bond.

According to the exemplary embodiment of the present specification, the nitrogen-containing heterocyclic compound represented by Chemical Formula 1 may be represented by any one of the following Chemical Formulas 2-1 to 2-22. However, the compound is not limited thereto. According to the exemplary embodiment of the present specification, the compounds represented by the following Chemical Formulas 2-1 to 2-22 may be unsubstituted or substituted by an additional substituent group.

Chemical Formula 2-1

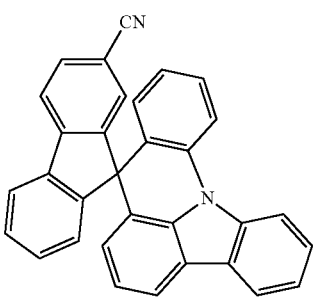

Chemical Formula 2-2

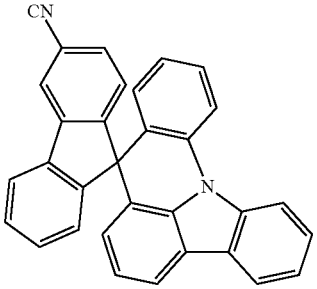

Chemical Formula 2-3

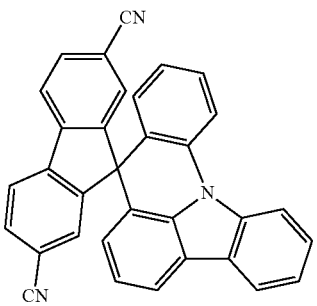

Chemical Formula 2-4
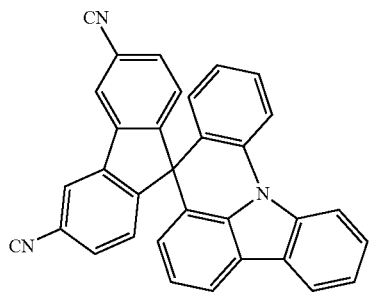
Chemical Formula 2-5
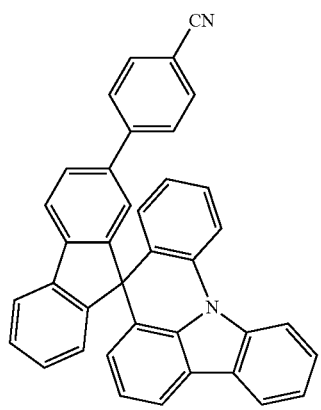
Chemical Formula 2-6
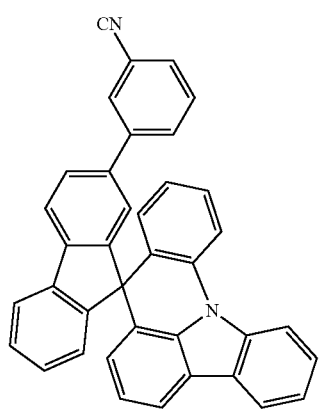
Chemical Formula 2-7
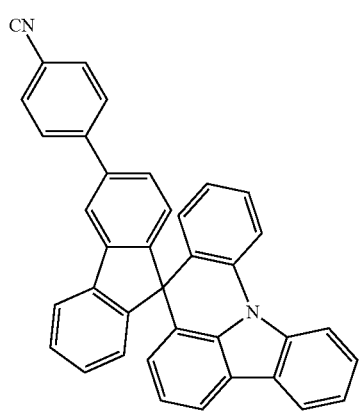
Chemical Formula 2-8
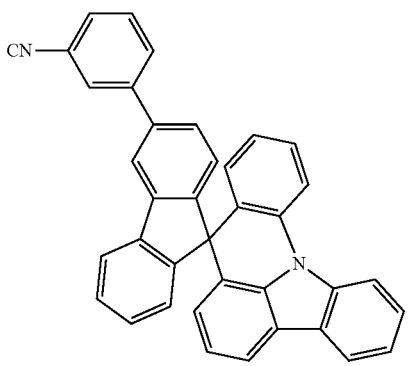
Chemical Formula 2-9
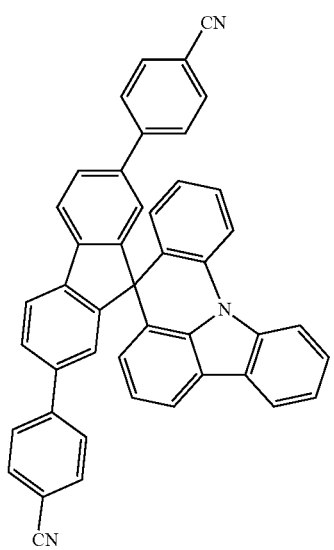
Chemical Formula 2-10
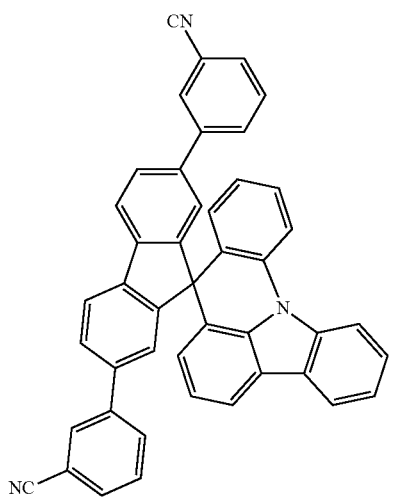

Chemical Formula 2-11
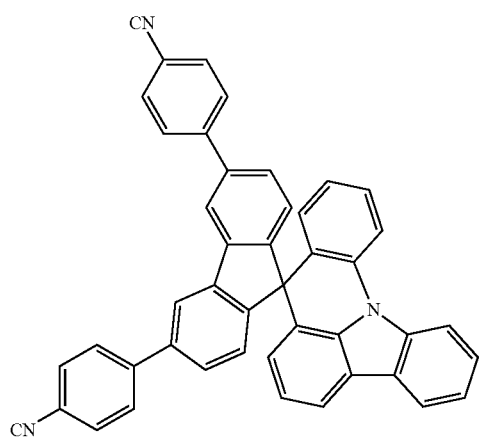
Chemical Formula 2-12
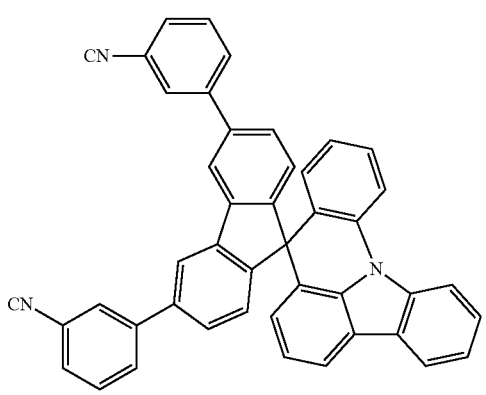
Chemical Formula 2-13
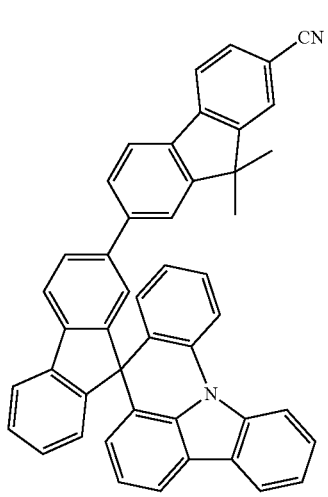
Chemical Formula 2-14
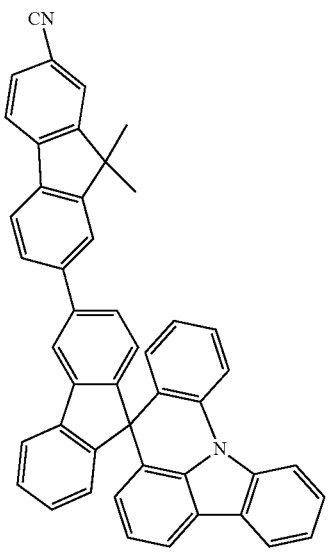
Chemical Formula 2-15
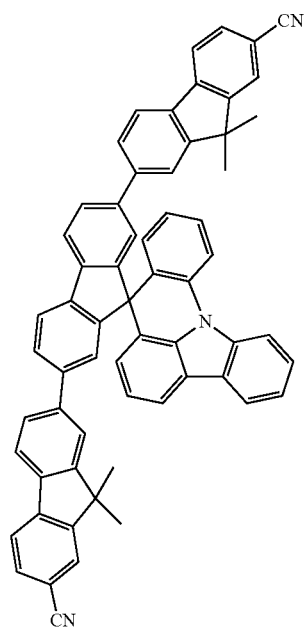

Chemical Formula 2-16
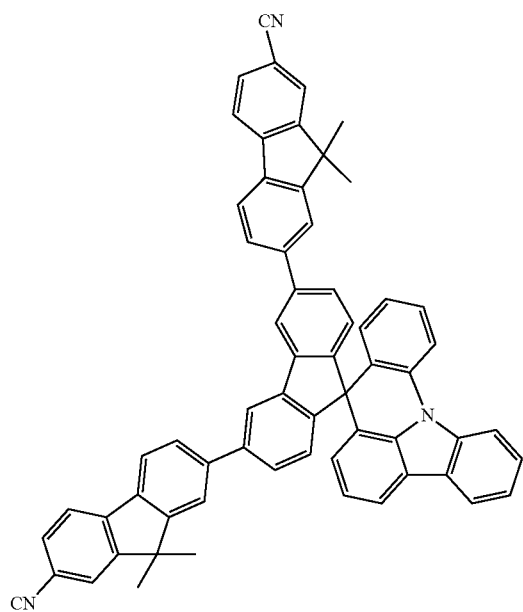
Chemical Formula 2-17
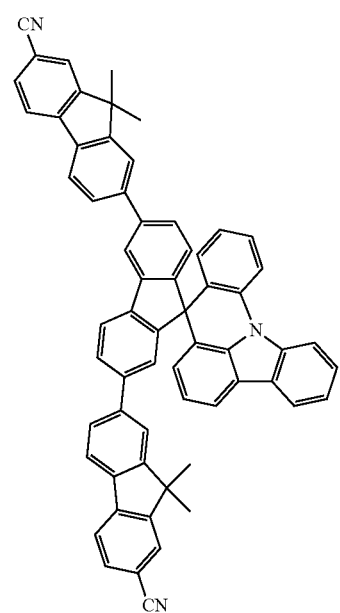
Chemical Formula 2-18
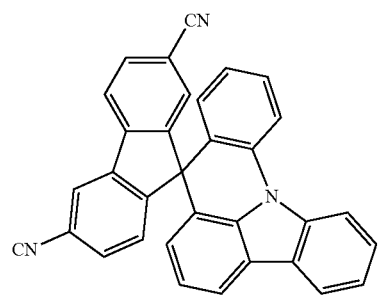
Chemical Formula 2-19
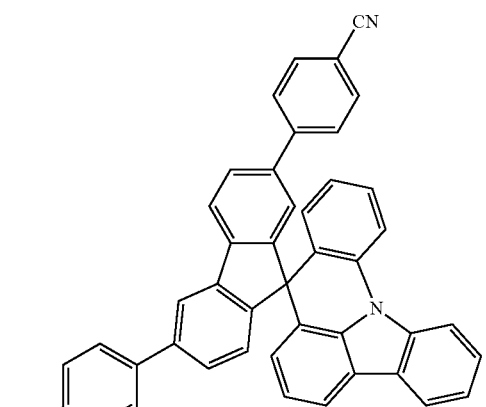
Chemical Formula 2-20
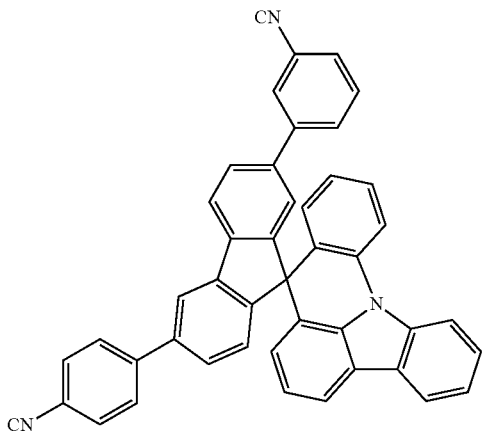
Chemical Formula 2-21
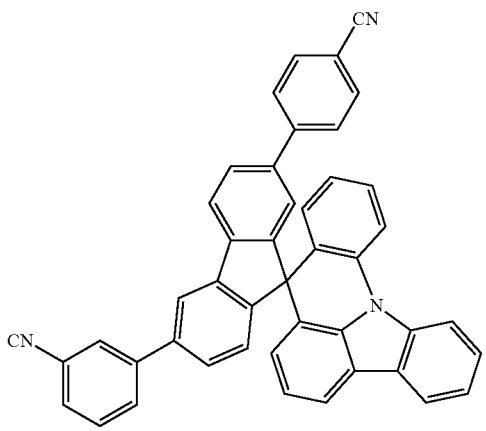

-continued

Chemical Formula 2-22

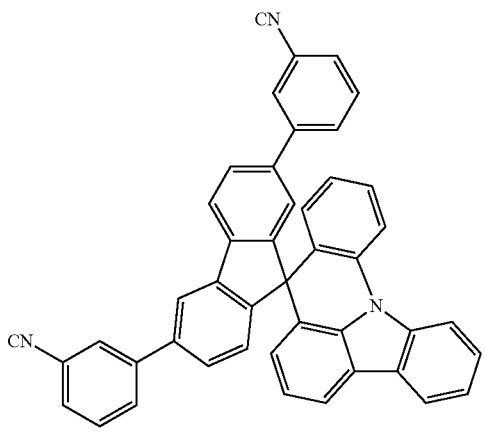

A starting material, a reaction material, a reaction condition, and the like may be changed based on Preparation Examples described below and the technology known in the art.

The exemplary embodiment of the present specification provides an organic electronic device including a first electrode; a second electrode facing the first electrode; and one or more organic material layers disposed between the first electrode and the second electrode, in which one or more of the organic material layers include the nitrogen-containing heterocyclic compound represented by Chemical Formula 1.

According to the exemplary embodiment of the present specification, the organic electronic device may be one selected from the group consisting of an organic solar cell, an organic light emitting device, and an organic transistor.

According to the exemplary embodiment of the present specification, the organic electronic device may be manufactured by depositing a metal, a metal oxides having conductivity, or an alloy thereof on a substrate by using a PVD (physical vapor deposition) method such as sputtering or e-beam evaporation to form an anode, forming the organic material layer including a hole injection layer, a hole transport layer, a light emitting layer, and an electron transport layer thereon, and depositing a material, which may be used as a cathode, thereon.

In addition to this method, the organic electronic device may be manufactured by sequentially depositing a cathode material, an organic material layer, and an anode material on a substrate (International Patent Application Laid-Open No. WO2003/012890). However, the manufacturing method is not limited thereto.

Further, according to the exemplary embodiment of the present specification, a smaller number of organic material layers may be manufactured by using various polymer materials and by using a solvent process instead of a deposition method, for example, a method such as spin coating, dip coating, doctor blading, screen printing, inkjet printing, or a heat transferring method.

According to the exemplary embodiment of the present specification, the organic material layer may have a multi-layered structure including a hole injection layer, a hole transport layer, a hole blocking layer, a light emitting layer, an electron blocking layer, an electron transport layer, and the like, but is not limited thereto and may have a single layer structure.

According to the exemplary embodiment of the present specification, the organic electronic device may be the organic light emitting device.

According to the exemplary embodiment of the present specification, the organic electronic device is an organic light emitting device including a first electrode; a second electrode facing the first electrode; and one or more organic material layers disposed between the first electrode and the second electrode, and one or more of the organic material layers may include the nitrogen-containing heterocyclic compound represented by Chemical Formula 1.

According to the exemplary embodiment of the present specification, the organic material layer may further include one or more selected from the group consisting of the light emitting layer, the hole transport layer, the hole blocking layer, the electron blocking layer, the electron transport layer, and the electron injection layer.

According to the exemplary embodiment of the present specification, the organic material layer includes the hole injection layer or the hole transport layer, and the hole injection layer or the hole transport layer may include the nitrogen-containing heterocyclic compound represented by Chemical Formula 1.

According to the exemplary embodiment of the present specification, the organic material layer may include the light emitting layer.

According to the exemplary embodiment of the present specification, the organic material layer includes the light emitting layer, and the light emitting layer may include the nitrogen-containing heterocyclic compound represented by Chemical Formula 1.

According to the exemplary embodiment of the present specification, the light emitting layer may include a host and a dopant.

According to the exemplary embodiment of the present specification, the host may include the nitrogen-containing heterocyclic compound represented by Chemical Formula 1.

According to the exemplary embodiment of the present specification, the dopant may include the nitrogen-containing heterocyclic compound represented by Chemical Formula 1.

According to the exemplary embodiment of the present specification, the organic material layer includes the electron transport layer, and the electron transport layer may include the nitrogen-containing heterocyclic compound represented by Chemical Formula 1.

According to the exemplary embodiment of the present specification, the organic material layer may include the hole injection layer or the hole transport layer including a compound including an arylamino group, a carbazole group, or a benzocarbazole group, in addition to the organic material layer including the nitrogen-containing heterocyclic compound represented by Chemical Formula 1.

According to the exemplary embodiment of the present specification, the organic material layer including the nitrogen-containing heterocyclic compound represented by Chemical Formula 1 may include the nitrogen-containing heterocyclic compound as the host, and another organic compound, a metal, or a metal compound as the dopant.

According to the exemplary embodiment of the present specification, the organic material layer may include a layer simultaneously performing electron transporting and light emission.

According to the exemplary embodiment of the present specification, the organic material layer may include a layer simultaneously performing light emission, and electron transporting and/or electron injection.

In the case where the organic light emitting device includes a plurality of organic material layers, the organic material layers may be formed of the same material or different materials.

According to the exemplary embodiment of the present specification, the organic electronic device may be the organic solar cell.

According to the exemplary embodiment of the present specification, the organic electronic device is an organic solar cell including a first electrode; a second electrode facing the first electrode; and one or more organic material layers provided between the first electrode and the second electrode and including a photoactive layer, and one or more of the organic material layers may include the nitrogen-containing heterocyclic compound represented by Chemical Formula 1.

According to the exemplary embodiment of the present specification, the organic material layer may include the photoactive layer.

According to the exemplary embodiment of the present specification, the photoactive layer may include the nitrogen-containing heterocyclic compound represented by Chemical Formula 1.

According to the exemplary embodiment of the present specification, the organic material layer may further include one or more selected from the group consisting of the photoactive layer, an electron donor, and an electron acceptor.

According to the exemplary embodiment of the present specification, the organic material layer may be a layer simultaneously having the electron donor and/or the electron acceptor as the photoactive layer.

According to the exemplary embodiment of the present specification, the organic material layer includes an electric charge generation layer, and the electric charge generation layer may include the heterocyclic compound represented by Chemical Formula 1.

According to the exemplary embodiment of the present specification, if the organic solar cell accepts a photon from an external light source, electrons and holes are generated between the electron donor and the electron acceptor. The generated holes may be transported through an electron donor layer to an anode.

According to the exemplary embodiment of the present specification, the organic material layer may include two kinds or more materials.

According to the exemplary embodiment of the present specification, the organic solar cell further includes an additional organic material layer. In the organic solar cell, the number of organic material layers may be reduced by using an organic material simultaneously having various functions.

According to the exemplary embodiment of the present specification, the organic material may include the electron donor and the electron acceptor, and the electron donor or the electron acceptor may include the nitrogen-containing heterocyclic compound.

According to the exemplary embodiment of the present specification, the organic electronic device may be the organic transistor.

According to the exemplary embodiment of the present specification, there is provided an organic transistor including a source, a drain, a gate, and one or more organic material layers.

According to the exemplary embodiment of the present specification, the organic electronic device is the organic transistor including the source, the drain, the gate, and one or more organic material layers, and one or more of the organic material layers may include the nitrogen-containing heterocyclic compound represented by Chemical Formula 1.

According to the exemplary embodiment of the present specification, the organic transistor may further include an insulating layer. The insulating layer may be positioned on the substrate and the gate.

According to the exemplary embodiment of the present specification, the organic material layer may include an electric charge generation layer, and the electric charge generation layer may include the nitrogen-containing heterocyclic compound represented by Chemical Formula 1.

The exemplary embodiment of the present specification provides a method of manufacturing an organic electronic device, including preparing a substrate; forming a first electrode on the substrate; forming an organic material layer including the nitrogen-containing heterocyclic compound represented by Chemical Formula 1 on the first electrode; and forming a second electrode on the organic material layer.

The substrate may be a glass substrate or a transparent plastic substrate having excellent transparency, surface smoothness, easiness in handling, and water resistance, but is not limited thereto, and there is no limitation as long as the substrate is a substrate generally used in the organic electronic device.

The first electrode may be the anode, and the second electrode may be the cathode.

The first electrode may become the cathode, the second electrode may become the anode.

In general, a material having a large work function so as to smoothly inject holes into the organic material layer is preferable as the anode. Specific examples of the anode material that can be used in the present invention include a metal such as vanadium, chrome, copper, zinc, and gold, or an alloy thereof; metal oxides such as zinc oxides, indium oxides, indium tin oxides (ITO), and indium zinc oxides (IZO); a combination of a metal and oxides such as ZnO:Al or $SnO_2$:Sb; and a conductive polymer such as poly(3-methylthiophene), poly[3,4-(ethylene-1,2-dioxy)thiophene] (PEDT), polypyrole, and polyaniline, but are not limited thereto.

In general, a material having a small work function so as to easily inject electrons into the organic material layer is preferably used as the cathode. Specific examples of the cathode material include a metal such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

In the case of the source, the drain, and the gate, the materials exemplified by the anode or the cathode may be used.

The material of the hole injection layer is a material that can well accept holes from the anode at a low voltage, and it is preferable that a HOMO (highest occupied molecular orbital) of the hole injection material be between the work function of the anode material and the HOMO of the surrounding organic material layer. Specific examples of the hole injecting material include metal porphyrin, oligothiophene, and arylamine-based organic materials; hexanitrile hexaazatriphenylene and quinacridone-based organic materials; perylene-based organic materials; anthraquinone, polyaniline, and polythiophene-based conductive polymers, and the like, but are not limited thereto.

The hole transport material is a material that can accept the holes from the anode or the hole injection layer and transfer the holes to the light emitting layer, and is preferably a material having large mobility for the holes. Specific examples thereof include an arylamine-based organic material, a conductive polymer, a block copolymer in which a conjugate portion and a non-conjugate portion are present together, and the like, but are not limited thereto.

The material of the light emitting layer is a material that can accept the holes and the electrons from the hole transport layer and the electron transport layer, respectively, and bond the holes and the electrons to emit light in a visible ray region, and is preferably a material having good quantum efficiency to fluorescence or phosphorescence. Specific examples thereof include a 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole, and benzimidazole-based compound; a poly(p-phenylenevinylene) (PPV)-based polymer; a spiro compound; polyfluorene; lubrene, and the like, but are not limited thereto.

The material of the electron transport layer is a material that can accept well the electrons from the cathode and transport the electrons to the light emitting layer, and is preferably a material having large mobility to the electrons. Specific examples thereof include an 8-hydroxyquinoline Al complex; a complex including $Alq_3$; an organic radical compound; a hydroxyflavone-metal complex, and the like, but are not limited thereto.

The organic electronic device according to the present specification may be a top emission type, a bottom emission type, or a both-sided emission type according to the used material.

Hereinafter, preferable Preparation Examples and Examples will be described in order to help understanding of the present invention. However, the following Preparation Examples and Examples are set forth to illustrate the present invention, but the scope of the present invention is not limited thereto.

Preparation Example 1

Preparation of Chemical Formula 2-3

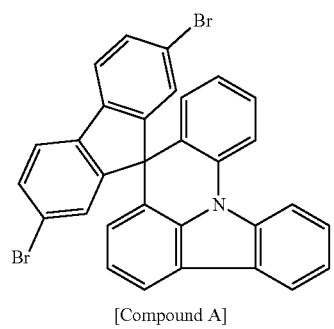

[Compound A]

-continued

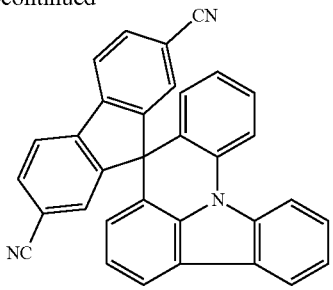

[Chemical Formula 2-3]

Compound A (20.0 g, 35.5 mmol) and CuCN (9.5 g, 107 mol) were agitated and refluxed in dimethylformamide (DMF) (150 mL) for 24 hours. 6N—HCl (50 ml) was slowly added at 100° C. The generated solid was filtered at room temperature. The solid was adsorbed on the silica gel and subjected to column to obtain Chemical Formula 2-3 (4.85 g, 30%).

MS: $[M+H]^+=455$

Figure 3:
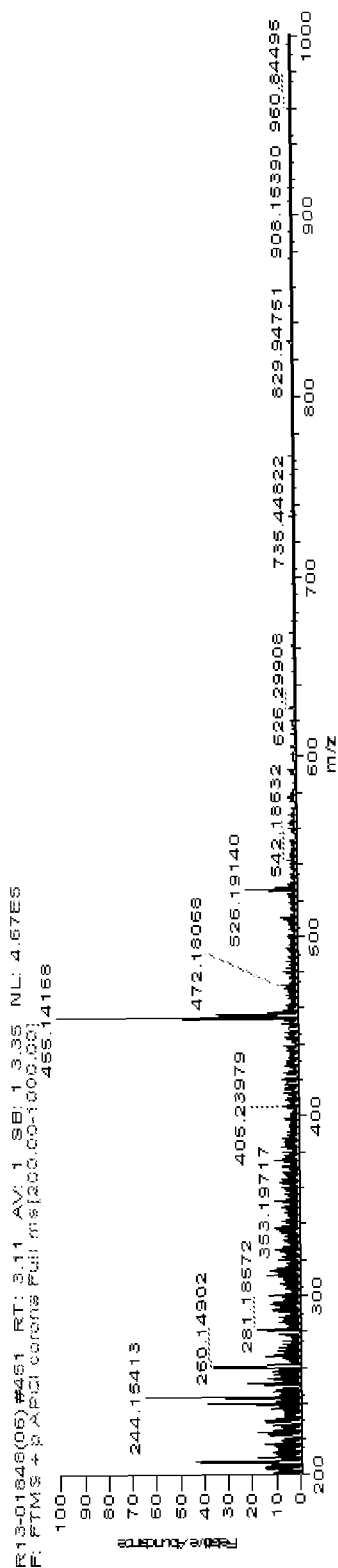
FIG. 3 illustrates a mass spectrum of Chemical Formula 2-3 prepared by Preparation Example 1 of the present specification.

FIG. 3 illustrates a mass spectrum of Chemical Formula 2-3 prepared by Preparation Example 1 of the present specification.

Preparation Example 2

Preparation of Chemical Formula 2-5

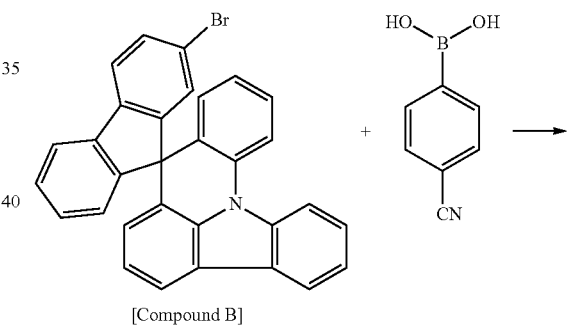

[Compound B]

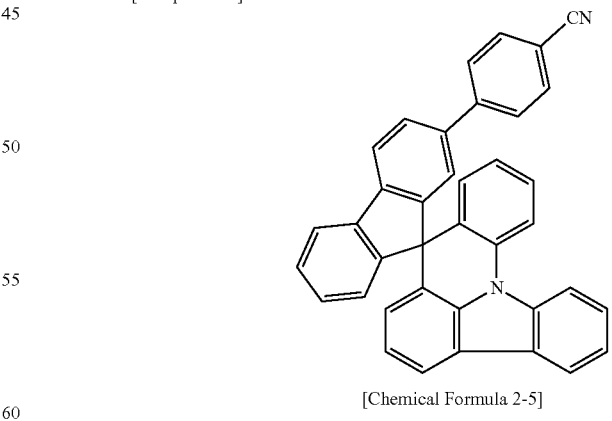

[Chemical Formula 2-5]

After compound B (12.0 g, 24.8 mmol) and 4-cyanophenylboronic acid (4.0 g, 27.3 mol) were completely dissolved in tetrahydrofurane (THF) (300 mL), 2M potassium carbonate aqueous solution (180 mL) was added thereto, and $Pd(PPh_3)_4$ (0.86 g, 3 mol %) was put thereinto, agitated and refluxed for 24 hours. The temperature was reduced to room temperature, the water layer was removed, and the organic layer was filtered. The solid was adsorbed on the silica gel and subjected to column to obtain Chemical Formula 2-5 (5.4 g, 43%).

MS: [M+H]$^+$=507

Figure 4:
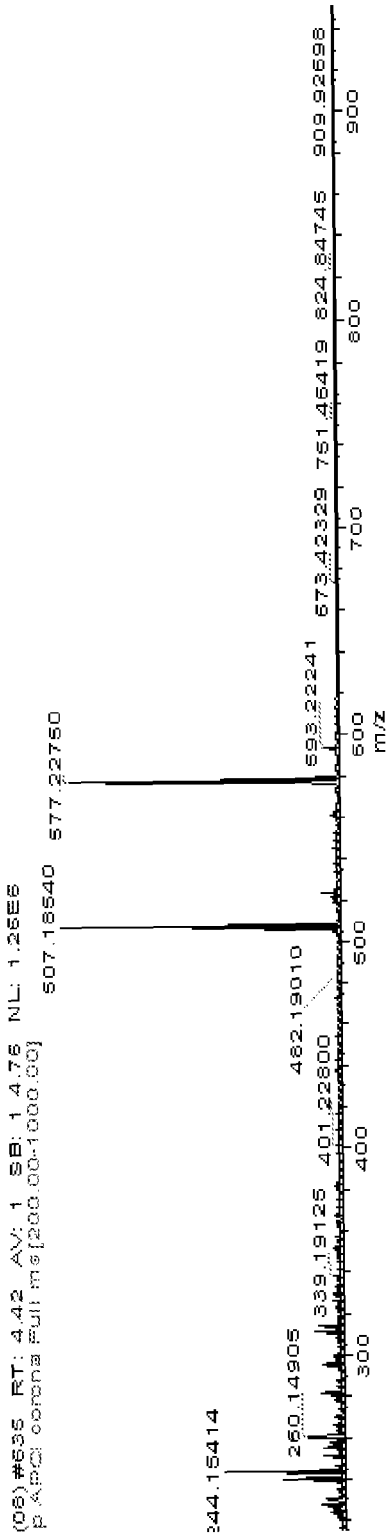
FIG. 4 illustrates a mass spectrum of Chemical Formula 2-5 prepared by Preparation Example 2 of the present specification.

FIG. 4 illustrates a mass spectrum of Chemical Formula 2-5 prepared by Preparation Example 2 of the present specification.

Preparation Example 3

Preparation of Chemical Formula 2-9

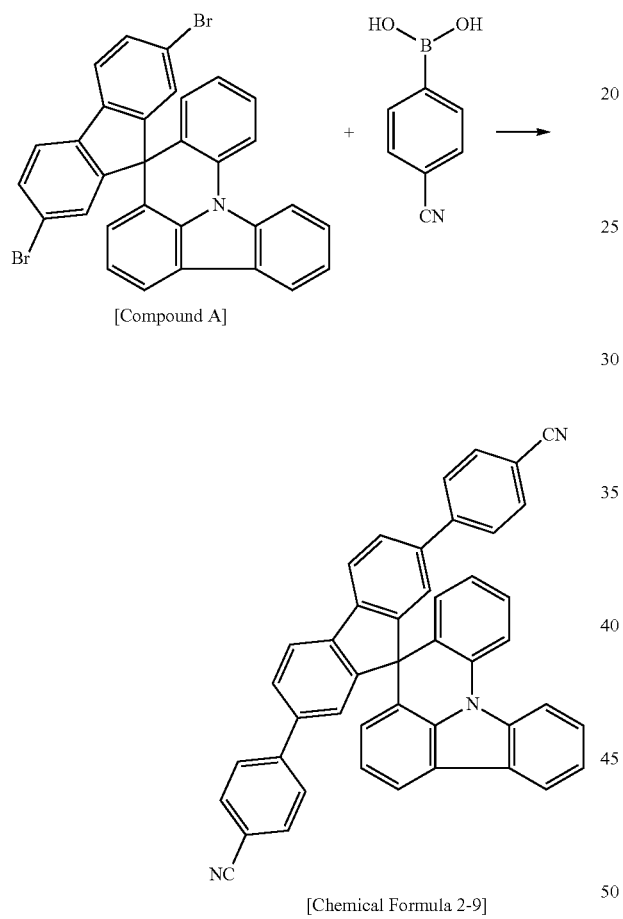

[Chemical Formula 2-9]

After compound A (12.0 g, 21.3 mmol) and 4-cyanophenylboronic acid (6.6 g, 44.7 mol) were completely dissolved in tetrahydrofurane (THF) (300 mL), 2M potassium carbonate aqueous solution (180 mL) was added thereto, and Pd(PPh$_3$)$_4$ (0.74 g, 3 mol %) was put thereinto, agitated and refluxed for 24 hours. The temperature was reduced to room temperature, the water layer was removed, and the organic layer was filtered. The solid was adsorbed on the silica gel and subjected to column to obtain Chemical Formula 2-9 (4.5 g, 35%).

MS: [M+H]$^+$=608

Figure 5:
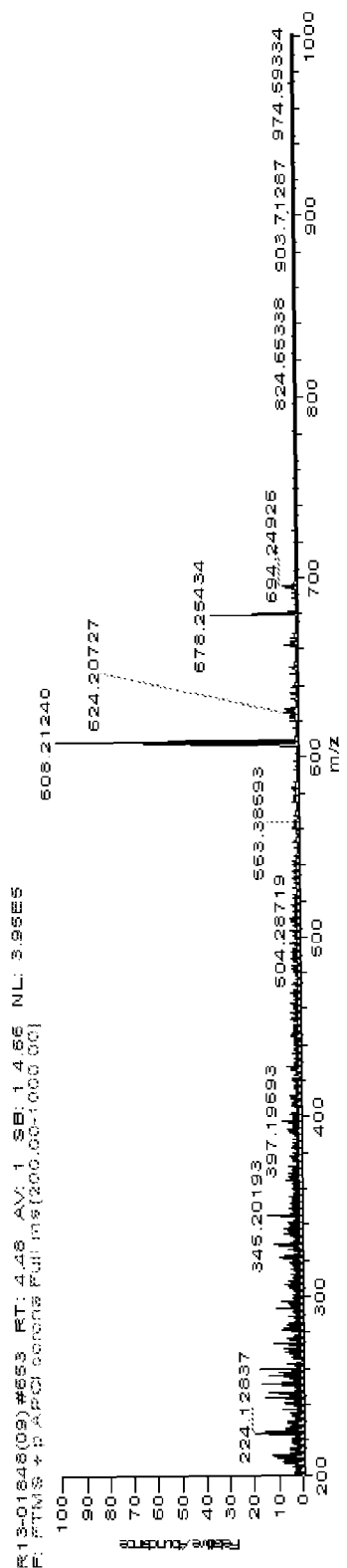
FIG. 5 illustrates a mass spectrum of Chemical Formula 2-9 prepared by Preparation Example 2 of the present specification.

FIG. 5 illustrates a mass spectrum of Chemical Formula 2-9 prepared by Preparation Example 3 of the present specification.

Preparation Example 4

Preparation of Chemical Formula 2-13

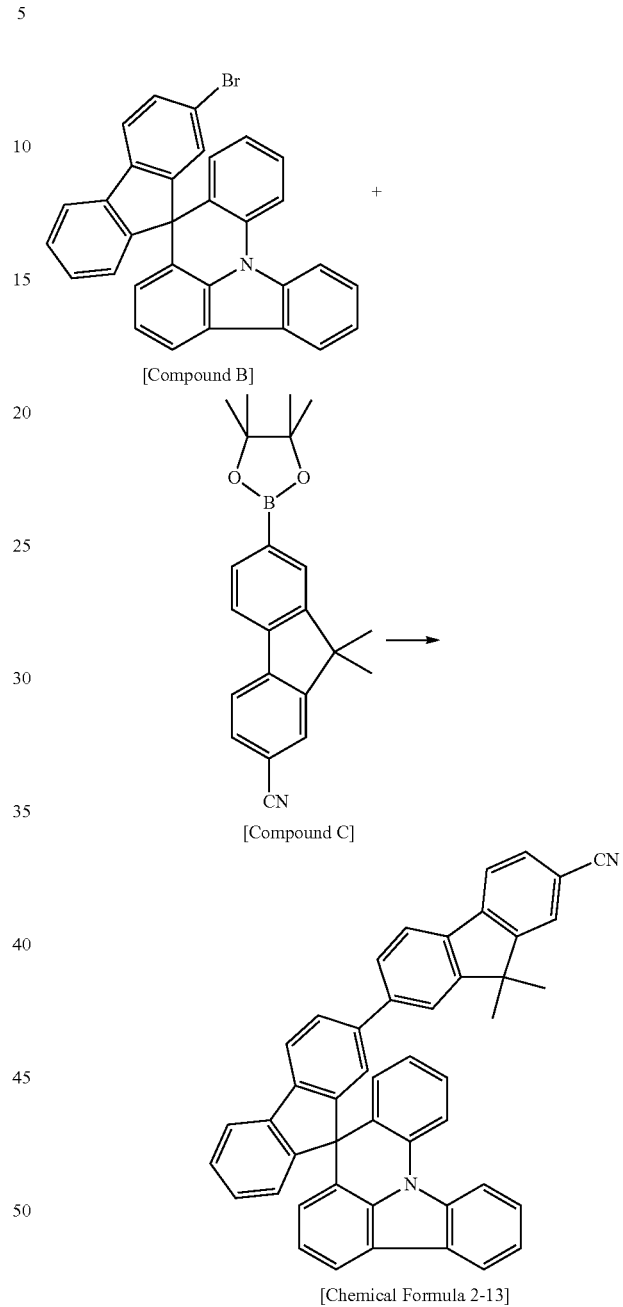

[Chemical Formula 2-13]

After compound B (8.7 g, 17.9 mmol) and compound C (6.8 g, 19.7 mol) were completely dissolved in tetrahydrofurane (THF) (300 mL), 2M potassium carbonate aqueous solution (180 mL) was added thereto, and Pd(PPh$_3$)$_4$ (0.4 g, 2 mol %) was put thereinto, agitated and refluxed for 24 hours. The temperature was reduced to room temperature, the water layer was removed, and the organic layer was filtered. The solid was adsorbed on the silica gel and subjected to column to obtain Chemical Formula 2-13 (4.6 g, 41%).

MS: [M+H]$^+$=623

Figure 6:
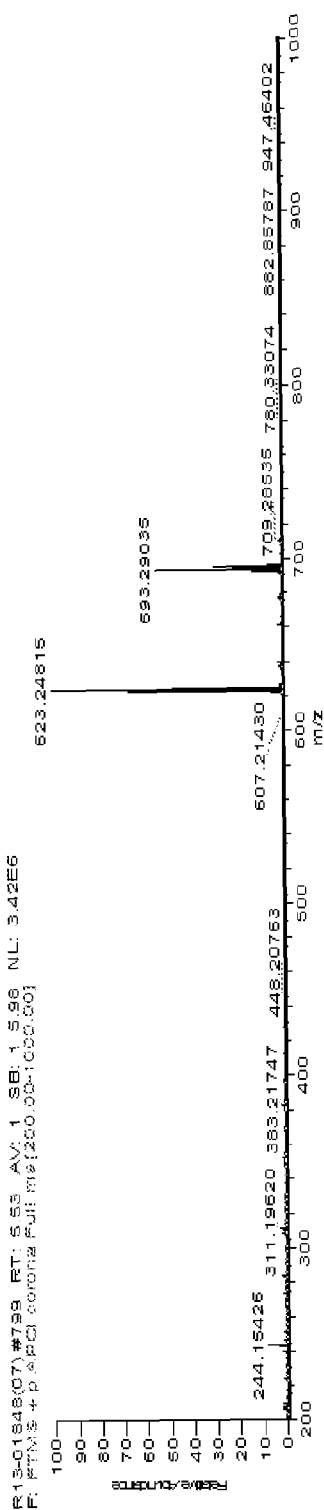
FIG. 6 illustrates a mass spectrum of Chemical Formula 2-13 prepared by Preparation Example 4 of the present specification.

FIG. 6 illustrates a mass spectrum of Chemical Formula 2-13 prepared by Preparation Example 4 of the present specification.

Preparation Example 5

Preparation of Chemical Formula 2-1

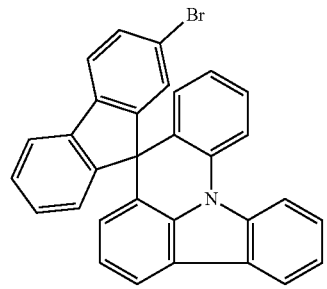

[Compound B]

+ CuCN ⟶

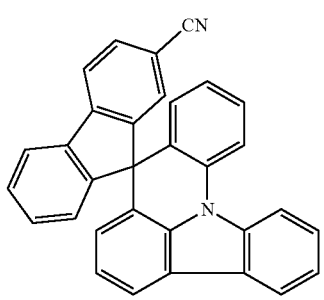

[Chemical Formula 2-1]

Compound B (10.0 g, 20.6 mmol) and CuCN (2.80 g, 31.0 mol) were agitated and refluxed in dimethylformamide (DMF) (150 mL) for 24 hours. 6N—HCl (50 ml) was slowly added at 100° C. The generated solid was filtered at room temperature. The solid was adsorbed on the silica gel and subjected to column to obtain Chemical Formula 2-1 (4.85 g, 30%).

Example 1

The glass substrate on which a thin film of ITO (indium tin oxide) was applied in a thickness of 500 Å was put into distilled water having the detergent dissolved therein and washed by the ultrasonic wave. In this case, the product manufactured by Fischer Co., was used as the detergent, and distilled water, which had been twice filtered by the filter manufactured by Millipore Co., was used as the distilled water. The ITO was washed for 30 minutes, and washing with ultrasonic waves was then repeated twice for 10 minutes by using distilled water. After the washing with distilled water was finished, washing with ultrasonic waves was performed by solvents such as isopropyl alcohol, acetone, and methanol, and the ITO was dried and transported to the plasma washing machine. Further, the substrate was washed by using oxygen plasma for 5 minutes, and then transported to the vacuum deposition machine.

Hexanitrile hexaazatriphenylene (HAT) of the following Chemical Formula was thermally deposited under vacuum in a thicknesses of 500 Å on the ITO transparent electrode thus prepared to form the hole injection layer.

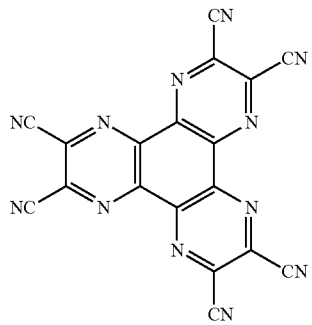

[HAT]

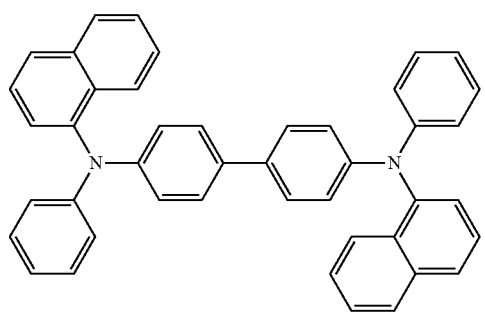

[NPB]

4,4'-bis[N-(1-naphthyl)-N-phenylamino]biphenyl (NPB) (250 Å), hexanitrile hexaazatriphenylene (HAT) (50 Å), and 4,4'-bis[N-(1-naphthyl)-N-phenylamino]biphenyl (NPB) (400 Å) of the aforementioned Chemical Formulas were sequentially deposited under vacuum on the hole injection layer to form the hole transport layer.

Subsequently, the prepared compound of Chemical Formula 2-3 and the dopant compound GD as below were deposited under vacuum at a weight ratio of 10:1 in a film thickness of 300 Å on the hole transport layer to form the light emitting layer.

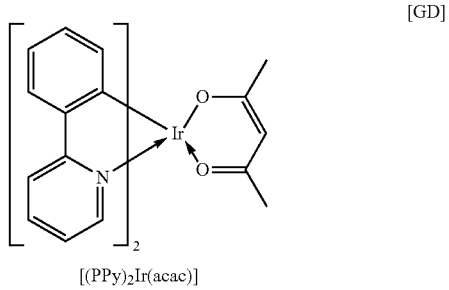

[GD]

[(PPy)$_2$Ir(acac)]

-continued

[ET-A]

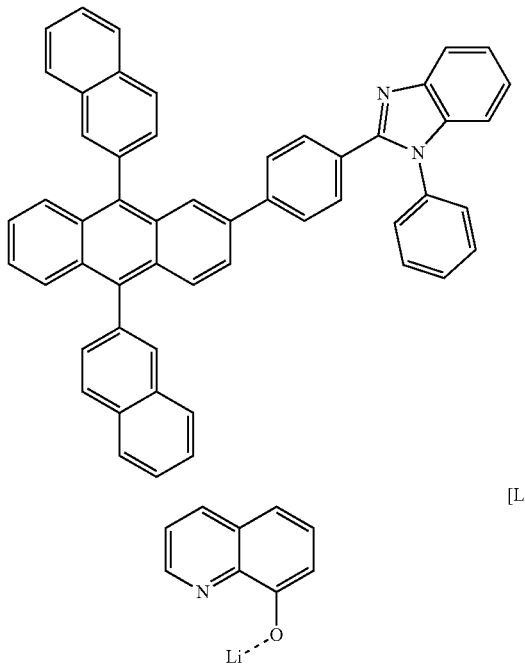

[LiQ]

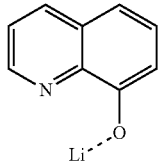

The compound of Chemical Formula ET-A as the material of the electron transport layer and Chemical Formula LiQ (lithium quinalate) were deposited under vacuum at a weight ratio of 1:1 on the light emitting layer to form the electron injection and transport layer in a thickness of 300 Å.

Lithium fluoride (LiF) in a thickness of 15 Å and aluminum in a thickness of 1,000 Å were subsequently deposited on the electron injection and transport layer to form the cathode.

In the aforementioned process, the deposition speed of the organic material was maintained at 0.4 to 0.7 Å/sec, the deposition speed of lithium fluoride of the cathode was maintained at 0.3 Å/sec, the deposition speed of aluminum was maintained at 2 Å/sec, and the degree of vacuum during deposition was maintained at $2 \times 10^{-7}$ to $5 \times 10^{-8}$ torr to manufacture the organic light emitting device.

Example 2

The organic light emitting device was manufactured by the same method as Example 1, except that the prepared compound of Chemical Formula 2-5 was used instead of the compound of Chemical Formula 2-3 of Example 1.

Example 3

The organic light emitting device was manufactured by the same method as Example 1, except that the prepared compound of Chemical Formula 2-9 was used instead of the compound of Chemical Formula 2-3 of Example 1.

Example 4

The organic light emitting device was manufactured by the same method as Example 1, except that the prepared compound of Chemical Formula 2-13 was used instead of the compound of Chemical Formula 2-3 of Example 1.

Comparative Example

The organic light emitting device was manufactured by the same method as the Examples, except that a compound of the following Chemical Formula GH-A was used instead of the compound synthesized in the aforementioned Examples.

[GH-A]

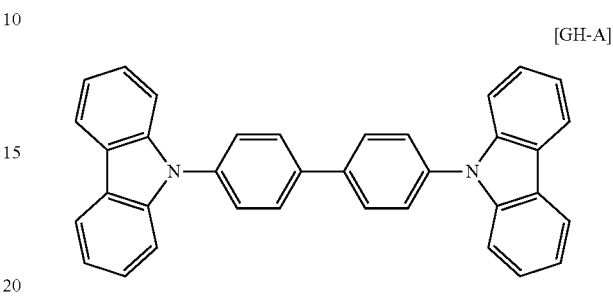

When the current (10 mA/cm$^2$) was applied to the organic light emitting devices manufactured in the Examples and Comparative Example 1, the results of Table 1 were obtained.

TABLE 1

| | Compound | Voltage (V) | Efficiency (cd/A) |
|---|---|---|---|
| Example 1 | Chemical Formula 2-3 | 3.50 | 62.3 |
| Example 2 | Chemical Formula 2-5 | 3.80 | 67.1 |
| Example 3 | Chemical Formula 2-9 | 3.29 | 60.7 |
| Example 4 | Chemical Formula 2-13 | 3.43 | 66.3 |
| Comparative Example 1 | GH-A | 6.12 | 15.26 |

From the results of Table 1, it can be seen that the novel compound according to the present invention may be used as a material of a light emitting layer of an organic electronic device including an organic light emitting device, and the organic electronic device including the organic light emitting device using the same exhibits excellent properties in views of efficiency, a driving voltage, stability and the like. Particularly, the compound may reduce the driving voltage and induce an increase in efficiency to improve power consumption.

The invention claimed is:

1. A nitrogen-containing heterocyclic compound represented by any one of the following Chemical Formulas 2-1 to 2-4, and 2-18:

Chemical Formula 2-1

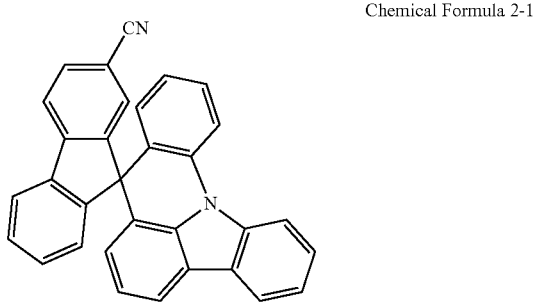

Chemical Formula 2-2

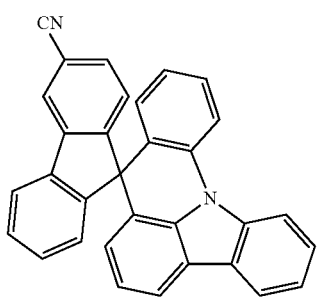

Chemical Formula 2-3

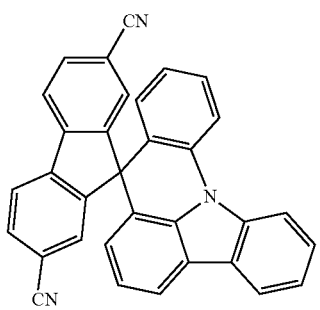

Chemical Formula 2-4

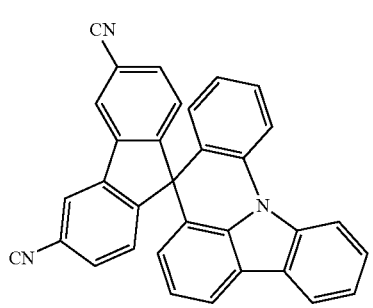

Chemical Formula 2-18

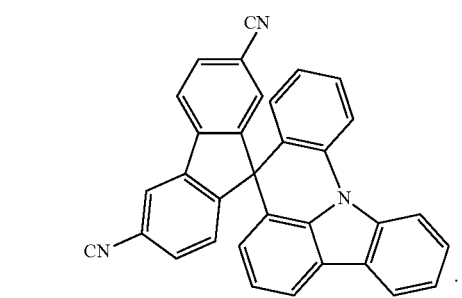

2. An organic electronic device comprising:
a first electrode;
a second electrode facing the first electrode; and
one or more organic material layers disposed between the first electrode and the second electrode,
wherein one or more of the organic material layers include the nitrogen-containing heterocyclic compound of claim 1.

3. The organic electronic device of claim 2, wherein the organic electronic device is selected from the group consisting of an organic solar cell, an organic light emitting device, and an organic transistor.

4. The organic electronic device of claim 2, wherein the organic electronic device is an organic light emitting device including a first electrode; a second electrode facing the first electrode; and one or more organic material layers disposed between the first electrode and the second electrode, and one or more of the organic material layers include the nitrogen-containing heterocyclic compound.

5. The organic electronic device of claim 4, wherein the organic material layer includes a hole injection layer or a hole transport layer, and the hole injection layer or the hole transport layer includes the nitrogen-containing heterocyclic compound.

6. The organic electronic device of claim 4, wherein the organic material layer includes a light emitting layer, and the light emitting layer includes the nitrogen-containing heterocyclic compound as a host of the light emitting layer.

7. The organic electronic device of claim 4, wherein the organic material layer includes an electron transport layer, and the electron transport layer includes the nitrogen-containing heterocyclic compound.

8. The organic electronic device of claim 4, wherein the organic material layer includes a hole injection layer or a hole transport layer including a compound including an arylamino group, a carbazole group, or a benzocarbazole group in addition to the organic material layer including the nitrogen-containing heterocyclic compound.

9. The organic electronic device of claim 4, wherein the organic material layer including the nitrogen-containing heterocyclic compound includes the nitrogen-containing heterocyclic compound as a host, and another organic compound, a metal, or a metal compound as a dopant.

10. The organic electronic device of claim 2, wherein the organic electronic device is an organic solar cell including a first electrode, a second electrode, and one or more organic material layers including a photoactive layer disposed between the first electrode and the second electrode, and one or more of the organic material layers include the nitrogen-containing heterocyclic compound.

11. The organic electronic device of claim 10, wherein the organic material layer includes an electric charge generation layer, and the electric charge generation layer includes the heterocyclic compound.

12. The organic electronic device of claim 10, wherein the organic material layer includes a photoactive layer, and the photoactive layer includes the nitrogen-containing heterocyclic compound.

13. The organic electronic device of claim 10, wherein the organic material layer includes an electron donor and an electron acceptor, and the electron donor or the electron acceptor includes the nitrogen-containing heterocyclic compound.

14. The organic electronic device of claim 2, wherein the organic electronic device is an organic transistor including a source, a drain, a gate, and one or more organic material layers, and one or more of the organic material layers include the nitrogen-containing heterocyclic compound.

15. The organic electronic device of claim 14, wherein the organic material layer includes an electric charge generation layer, and the electric charge generation layer includes the nitrogen-containing heterocyclic compound.

16. A method of manufacturing an organic electronic device, comprising:
preparing a substrate;
forming a first electrode on the substrate;
forming an organic material layer including the nitrogen-containing heterocyclic compound of claim 1 on the first electrode; and
forming a second electrode on the organic material layer.

* * * * *